United States Patent
Ahlberg et al.

(10) Patent No.: US 8,734,484 B2
(45) Date of Patent: May 27, 2014

(54) SYSTEM AND METHOD FOR CLOSURE OF AN INTERNAL OPENING IN TISSUE, SUCH AS A TRANS-APICAL ACCESS OPENING

(75) Inventors: Sarah Ahlberg, Crystal, MN (US); Sara Simma, St. Paul, MN (US); Paul T. Rothstein, Elk River, MN (US); Martin Clements, Rogers, MN (US); Damian Jelich, Cottage Grove, MN (US); Timothy G. Laske, Shoreview, MN (US); Cynthia Clague, Minnetonka, MN (US); Michael Green, Forest Lake, MN (US); Paul Iaizzo, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 407 days.

(21) Appl. No.: 12/427,395

(22) Filed: Apr. 21, 2009

(65) Prior Publication Data
US 2010/0268253 A1   Oct. 21, 2010

(51) Int. Cl.
| A61B 17/03 | (2006.01) |
| A61B 17/122 | (2006.01) |
| A61B 17/128 | (2006.01) |
| A61F 2/24 | (2006.01) |

(52) U.S. Cl.
USPC .......... 606/216; 623/2.11; 606/142; 606/151; 606/232

(58) Field of Classification Search
USPC ......... 606/139, 142, 216, 217, 219, 232, 151, 606/157; 623/2.11, 2.36, 2.41, 904; 604/500
See application file for complete search history.

(56) References Cited

U.S. PATENT DOCUMENTS

| 6,203,554 B1 | 3/2001 | Roberts |
| 6,702,826 B2 * | 3/2004 | Liddicoat et al. ............. 606/151 |
| 6,913,607 B2 | 7/2005 | Ainsworth et al. |
| 6,918,917 B1 | 7/2005 | Nguyen et al. |
| 6,986,775 B2 | 1/2006 | Morales et al. |
| 7,001,412 B2 | 2/2006 | Gallagher et al. |

(Continued)

FOREIGN PATENT DOCUMENTS

| WO | 03/088875 A1 | 10/2003 |
| WO | 2007/047851 A2 | 4/2007 |
| WO | 2007/089431 A1 | 8/2007 |
| WO | 2007/089843 A2 | 8/2007 |

OTHER PUBLICATIONS

PCT Search Report (PCT/US2010/031074) dated Dec. 10, 2010 (5 page).

(Continued)

*Primary Examiner* — Kathleen Holwerda
*Assistant Examiner* — Sarah W Aleman

(57) ABSTRACT

A method for closing an opening at a target site including bodily tissue including embedding a plurality of self-closing clips into the target site in a spaced apart manner about a perimeter of the opening. Each of the clips has opposing clip ends and an intermediate segment. A flexible tether is coupled to the embedded clips to form a loop about the opening perimeter. A pulling force is applied onto at least one of the loop ends, thereby drawing the perimeter of the opening onto itself to completely close the opening. The loop ends are secured to maintain the target site in a closed state. In some embodiments, the target site is apical cardiac tissue, and the method is performed as part of a trans-apical access procedure.

18 Claims, 17 Drawing Sheets

(56) References Cited

U.S. PATENT DOCUMENTS

| | | | |
|---|---|---|---|
| 7,166,127 B2 | 1/2007 | Spence et al. | |
| 7,276,078 B2 | 10/2007 | Spenser et al. | |
| 8,163,010 B1* | 4/2012 | Hausen et al. | 623/2.32 |
| 2003/0233142 A1 | 12/2003 | Morales et al. | |
| 2004/0186486 A1* | 9/2004 | Roue et al. | 606/139 |
| 2005/0021054 A1 | 1/2005 | Ainsworth et al. | |
| 2005/0080454 A1* | 4/2005 | Drews et al. | 606/221 |
| 2005/0234512 A1 | 10/2005 | Nakao | |
| 2005/0267571 A1* | 12/2005 | Spence et al. | 623/2.11 |
| 2006/0190030 A1* | 8/2006 | To et al. | 606/205 |
| 2007/0027534 A1 | 2/2007 | Bergheim et al. | |
| 2007/0112422 A1* | 5/2007 | Dehdashtian | 623/2.11 |
| 2008/0004640 A1 | 1/2008 | Ellingwood | |
| 2008/0234815 A1 | 9/2008 | Starksen | |
| 2008/0249504 A1 | 10/2008 | Lattouf et al. | |

OTHER PUBLICATIONS

J. Ernesto Molina, "Surgical Options for Endocardial Lead Placement When Upper Veins are Obstructed or Nonusable"; Journal of Interventional Cardiac Electrophysiology 11, 149-154, 2004.

* cited by examiner

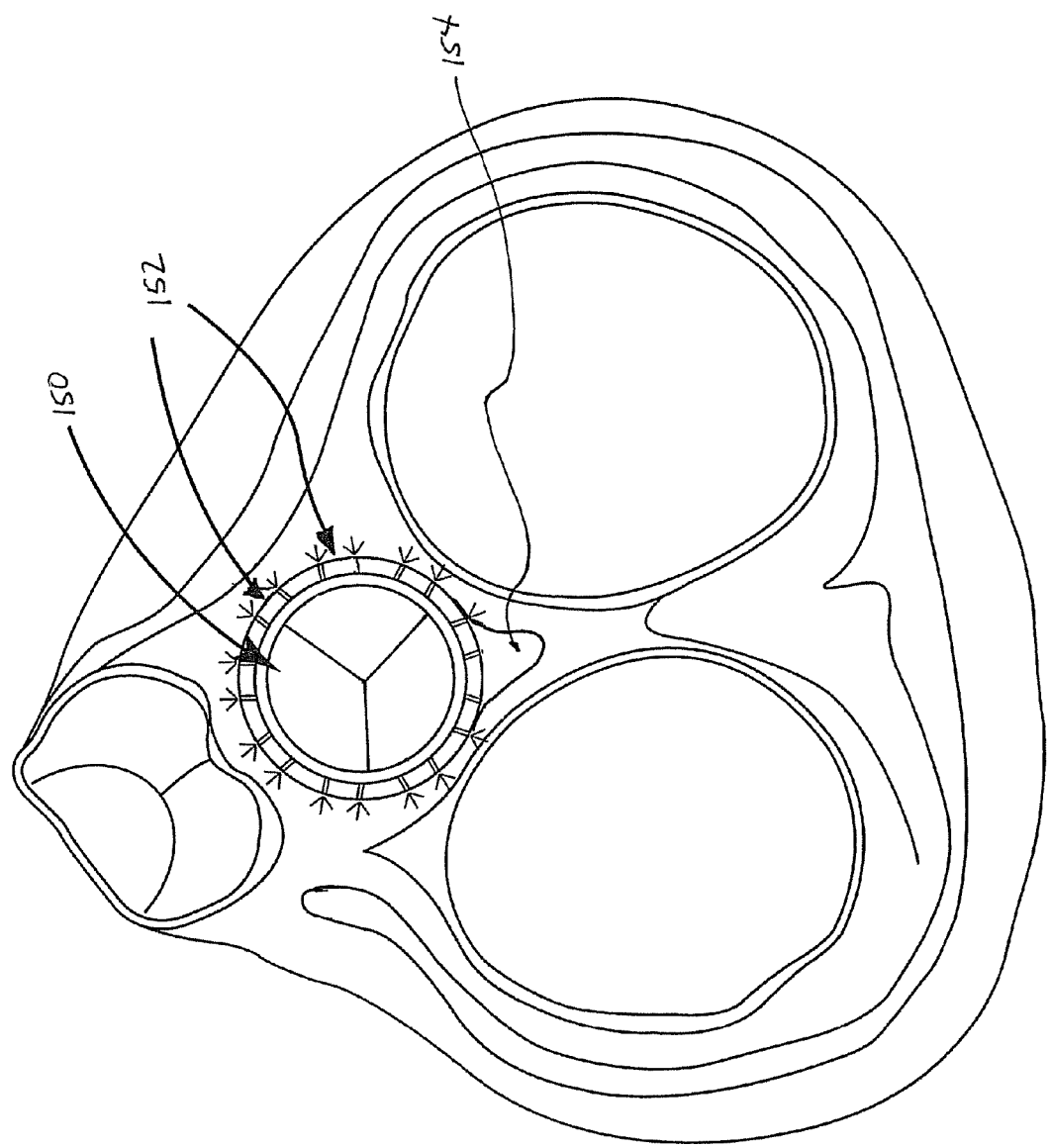

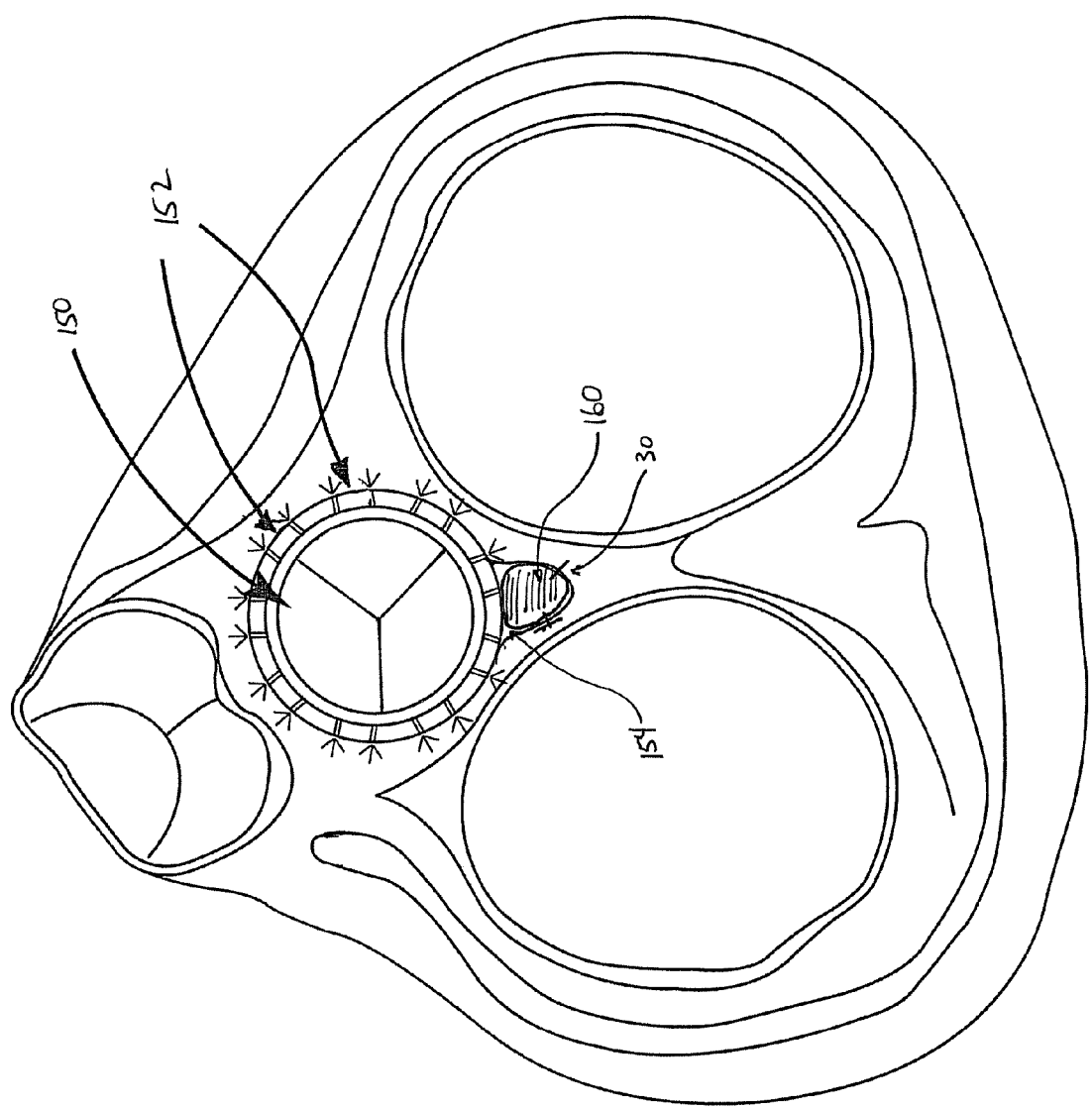

SYSTEM AND METHOD FOR CLOSURE OF AN INTERNAL OPENING IN TISSUE, SUCH AS A TRANS-APICAL ACCESS OPENING

BACKGROUND

The present disclosure relates to surgical systems and procedures for closing an orifice or other opening in bodily organs, vessels, or other tissue. More particularly, it relates to devices and methods that are amenable to minimally invasive surgical procedures, and are readily deployed in manners facilitating closure of an internal opening.

The need to surgically proximate and close an opening in tissue arises under a plethora of difference circumstances. Tissue defects, such as wounds, are one such example. Treatment of a skin surface wound typically entails suturing edges of the wound together. In many instances, however, the tissue opening to be treated is internally located, and thus not readily accessible by a surgeon otherwise attempting to utilize a conventional suture thread to effectuate repair of the opening. Access to internal tissue openings of these types through invasive surgery introduces a high level of risk that can result in serious complications for the patient, especially where the opening or orifice in question is located at or near a vital organ. One example of an internal tissue opening of this type is a trans-apical orifice formed through a wall of the heart at the ventricular apex.

By way of reference, various medical procedures on the heart can be performed inside the heart (endocardial) and on the outside of the heart (epicardial). Endocardial procedures require access to the interior of the heart, which can be accomplished percutaneously through the vasculature or directly through the patient's chest and heart wall. With direct access techniques, a conventional location at which the interior of the heart is accessed is via an opening formed at the ventricular apex of the heart, commonly referred to as trans-apical access. For example, trans-apical prosthetic heart valves have recently been developed that are delivered to the native heart valve to be repaired via a transcatheter approach in which the catheter is inserted through an opening made at the ventricular apex. Other endocardial procedures similarly entail forming an access opening through a wall of the heart, and can include other cannula-like instruments being inserted through the access opening. Upon completion of the procedure (and removal of the catheter or other cannula-like device), the access opening must be closed. Conventionally, sutures are employed; however, manually sewing a suture to the cardiac tissue can be time-consuming and difficult, especially with minimally invasive and/or transcatheter procedures. Alternatively, it has been suggested that a plug can be inserted into the heart wall opening. Unfortunately, complete closure may be difficult to achieve, and additional procedures must be performed (e.g., manually sewn suture) to secure the plug to the cardiac tissue.

Cardiac apical access openings are but one example of an internal opening or orifice requiring surgical closure. Paravalvular leaks, vessel repair, gastric incisions, etc., present similar concerns. While manual suturing of the opening is well-accepted, in many instances this technique is less than optimal. Therefore, a need exists for systems and methods for closing an internal bodily opening or orifice, such as an apical heart wall opening.

SUMMARY

Some aspects in accordance with principles of the present disclosure relate to a method for closing an opening at a target site including bodily tissue. The method includes embedding a plurality of self-closing clips into the target site in a spaced apart manner about a perimeter of the opening. The clips each have opposing clip ends and an intermediate segment extending between the clip ends. A flexible tether is coupled to the intermediate section of each of the embedded clips to form a loop about an entirety of the perimeter of the opening, the loop terminating at opposing loop ends. A pulling force is applied onto at least one of the loop ends, with the pulling force being transposed onto the embedded clips to thereby draw the perimeter of the opening onto itself to completely close the opening. Thus, the pulling force transitions the target site from the open state to a closed state. Finally, the loop ends are secured so as to maintain the target site in the closed state. In some embodiments, the target site is apical cardiac tissue, and the method is performed as part of a trans-apical access procedure. For example, the clips can be embedded into the epicardial surface and the tether coupled thereto prior to forming the access opening; subsequently, the access opening is formed within the loop and a surgical tool passed therethrough for accessing an interior of the heart. Upon completion of the procedure and removal of the tool, the access opening is closed by tightening the tether. In other embodiments, the target site includes a native heart valve annulus, and the opening is between the native annulus and an implanted prosthetic heart valve.

Other aspects in accordance with principles of the present disclosure relate to a system for closing an opening at a target site including bodily tissue. The system includes a plurality of clip assemblies and a tether. The clip assemblies each include a self-closing clip and a clasp. The clip is defined by opposing leg segments and an intermediate segment, each of the leg segments terminating at a piercing end. In this regard, each of the clips are self-transitionable from a deflected state to a natural state in which the leg segments are curved in extension from the intermediate segment, and the intermediate segment is relatively straight. The deflected state, on the other hand, includes the leg segments approaching a straightened shape. The clasp is coupled to the intermediate segment. Finally, the flexible tether extends between and interconnects each of the clasps. With this configuration, the system is readily deployed to facilitate closure of an internal bodily opening or orifice. In some embodiments, the flexible tether is slidably coupled to each of the clasps, and the system further includes a delivery tool configured to maintain the clips in the deflected state (and optionally the flexible tether), and to substantially simultaneously deploy the clip assemblies.

Yet other aspects in accordance with principles of the present disclosure relate to a method for sealing a paravalvular leak formed by a cavity between an implanted prosthetic valve and a native heart valve annulus. The method includes inserting a homogenous plug body into the cavity. At least one self-closing clip is deployed in the plug body and tissue of the native annulus to secure the plug body to the tissue. In some embodiments, the plug body is sponge, Dacron, or foam.

BRIEF DESCRIPTION OF THE DRAWINGS

FIG. 8A is a simplified view of another target site including a prosthetic heart valve implanted to a native heart valve annulus and having a paravalvular leak;

FIG. 8D illustrates another system in accordance with principles of the present disclosure for closing the paravalvular leak of the target site of FIG. 8A;

DETAILED DESCRIPTION

The present disclosure provides, in some aspects, a system and method for closing openings in bodily tissues that is both effective and compatible with many of the tools and techniques employed in minimally invasive surgery. Although aspects of the present disclosure will be described in connection with closing a trans-apical heart wall access opening, it should be understood that the system has other applications. It may be adapted to be used on other bodily tissues or organs to facilitate closure of other types of openings, wounds, orifices, etc., as would be apparent to those of skill.

According to one aspect of the present disclosure, a surgical system including a plurality of self-closing clips are deployed about a target site opening, and are connected to one another by a flexible tether. In response to a pulling force applied to the tether, the clips collectively draw a perimeter of the opening toward itself to effectuate closure of the opening.

Figure 1:
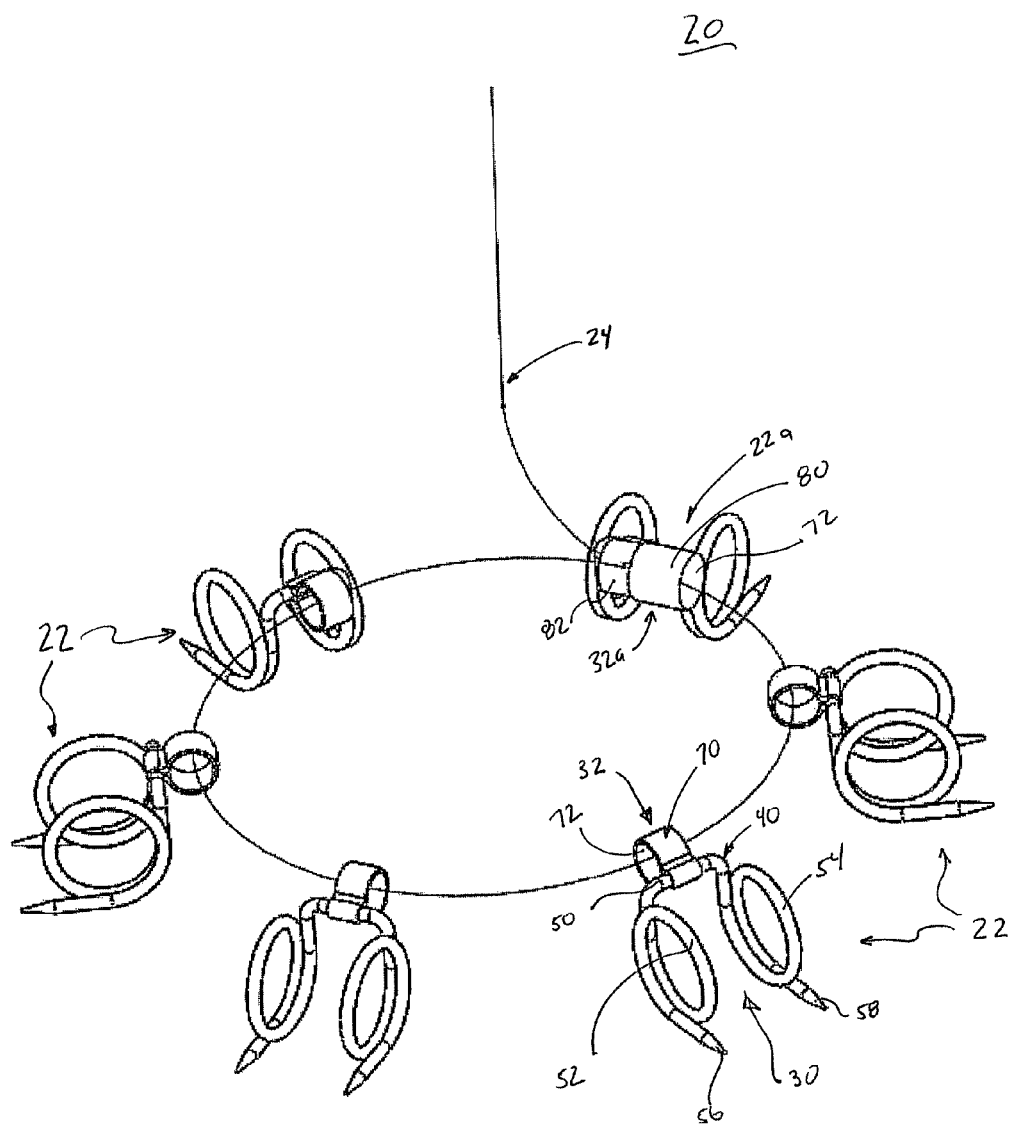
FIG. 1 is a perspective view of a closure system in accordance with principles of the present disclosure for closing an internal opening in tissue.

With the above understanding in mind, one construction of a system 20 for closing an opening at an internal bodily target site is shown in FIG. 1, and includes a plurality of clip assemblies 22 and a flexible tether 24. Details on the various components are provided below. In general terms, however, the clip assemblies 22 are configured for deployment into tissue, and are connected to one another via the tether 24. A pulling force applied to the tether 24 draws the clip assemblies 22 toward one another, and thus any tissue or other structures otherwise attached to the corresponding clip assembly 22. Although FIG. 1 depicts the closure system 20 as including six of the clip assemblies 22, any other number, either greater or lesser, is also acceptable.

The clip assemblies 22 can assume a wide variety of forms, and in some embodiments are identical. Each of the clip assemblies 22 includes a self-closing clip 30 and an optional coupling body 32. Where provided, the coupling body 32 is configured to receive the tether 24, thereby coupling the tether 24 with the corresponding self-closing clip 30. Alternatively, the tether 24 can be directly connected to or about a component of each of the self-closing clips.

In general, the self-closing clip 30 includes a shape memory member 40 that can have a closed memory set configuration as shown in FIG. 1, and is transitionable from the natural or undeformed state reflected in FIG. 1 to a biased or deflected state, and then self-revert back to the natural or undeformed state. In this regard, deployment of the clip assemblies 22 are, in some embodiments, premised upon a shape memory attribute of the member 40. For example, the self-closing clip 30 can exhibit a loop-shaped memory set shape or configuration and includes, in the natural state shown, an intermediate segment or bridge 50 interconnecting opposing leg or end segments 52, 54. In the natural undeformed state of FIG. 1, each of the leg segments 52, 54 forms an overlapping loop, although in other embodiments, the loop-like shape can be non-overlapping. The shape memory member 40 can be Nitinol wire and provided with a desired memory set configuration to exhibit pseudo elastic (super elastic) behavior. In other words, at least a portion of the shape memory alloy is converted from its austenitic phase to its martensitic phase when the wire is in its deformed configuration. As the stress is removed, the material undergoes a martensitic to austenitic conversion and springs back (e.g., self-reverts) to its original or undeformed or undeflected configuration.

Each of the leg segments 52, 54 terminate at an end 56, 58, respectively, opposite the intermediate segment 50 that are, in some embodiments, sharpened to promote piercing of target tissue (not shown) or other structures. Alternatively, one or both of the end(s) 56 and/or 58 can be blunt. Additional examples of self-closing clips useful with the present disclosure are described in U.S. Pat. No. 6,926,730 entitled "Minimally Invasive Valve Repair Procedure and Apparatus"; U.S. application Ser. No. 09/828,322 filed Apr. 5, 2001 and entitled "Bridge Clip Tissue Connector Apparatus and Methods"; and U.S. application Ser. No. 12/401,183 filed Mar. 10, 2009 and entitled "Apparatus and Methods for Minimally Invasive Valve Repair"; an entirety of the teachings of each of which are incorporated herein by reference.

The optional coupling body 32, where provided, can also assume a variety of forms, and in some embodiments includes a clasp 70 assembled to and extending from the intermediate segment 50 of the corresponding self-closing clip 30. The clasp 70 form an open-ended passage 72 sized to slidably capture or receive the flexible tether 24. In some embodiments, the coupling bodies 32 are identical. In other embodiments, however, one or more of the clip assemblies 22 can incorporate a differently-configured coupling body 32. For example, with respect to the clip assembly 22a identified in FIG. 1, the corresponding coupling body 32a includes a first portion 80 and a second portion 82. The first portion 80 is akin to the clasps 70 described above, and forms the open-ended passage 72 through which the tether 24 is slidably retained. The second portion 82 is configured to more permanently attach the tether 24 for reasons made clear below. With this but one acceptable construction, an outer diameter of the second portion 82 can be less than a diameter of the passage 72 of the first portion 80 such that the tether 24 can extend about the second portion 82 in establishing the sliding interface relative to the first portion 80.

Regardless of an exact construction, the coupling body 32, where provided, is substantially rigid, and is permanently assembled to the corresponding self-closing clip 30. With this construction, a force applied to the coupling body 32 is directly transposed onto the corresponding self-closing clip 30, and the coupling body 32 will not overtly deform in response to expected forces during use (e.g., pulling force applied to the tether by an adult).

The flexible tether 24 can assume a variety of forms, and in some constructions is a suture. The flexible tether 24 can be one long piece of material, or two or more pieces, and can comprise any suture-like material, a Dacron strip, or the like.

Figure 2A:
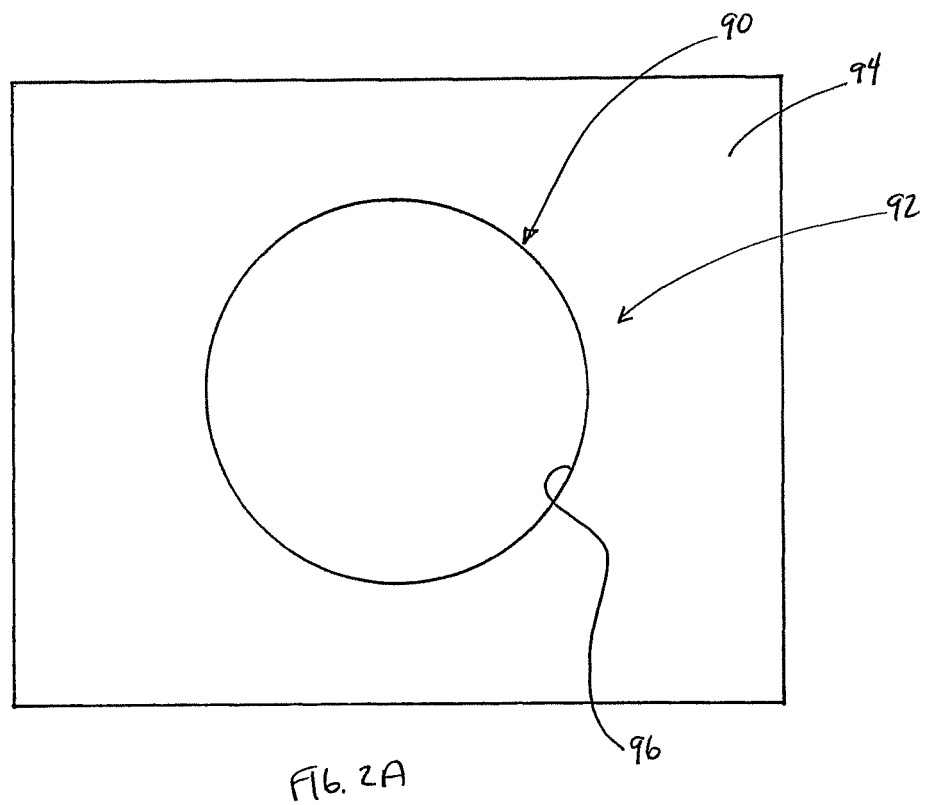
FIG. 2A is a simplified, plan view of a tissue target site including an opening for which the system of FIG. 1 is useful in closing.
Figure 2B:
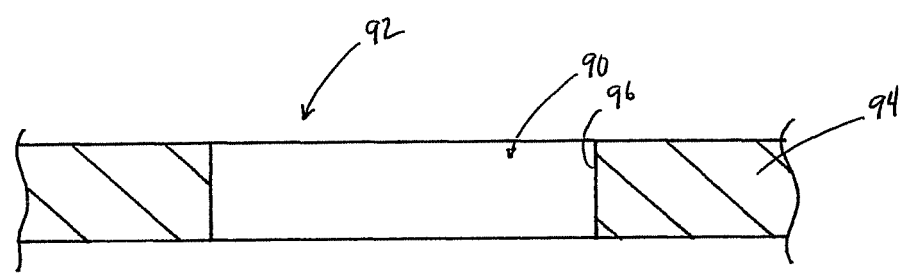
FIG. 2B is a cross-sectional view of the target site of FIG. 2A.
Figure 3A:
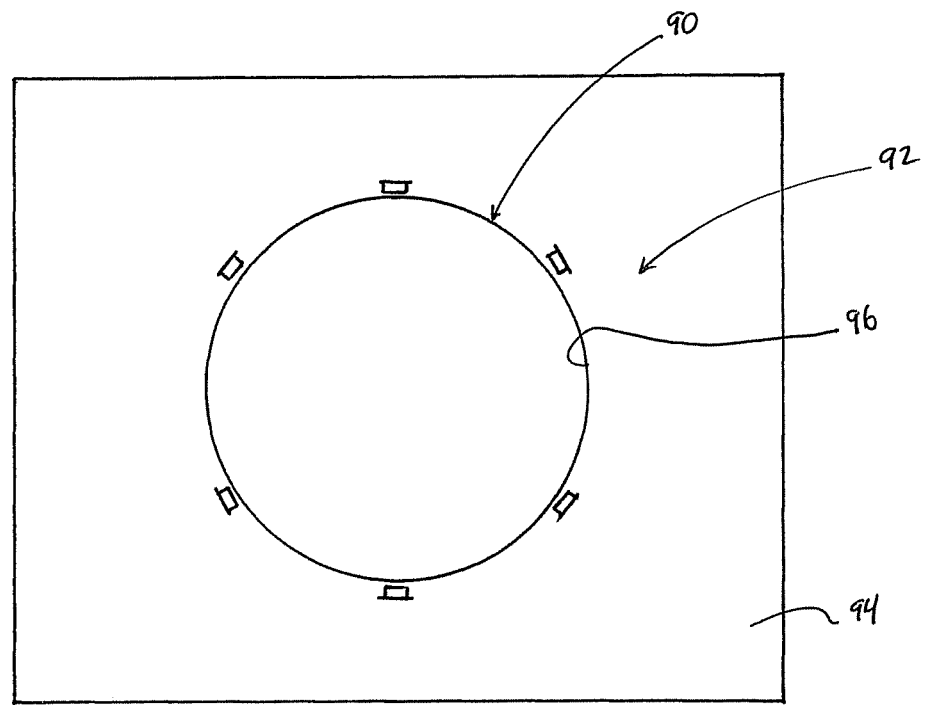
FIG. 3A is a plan view of the target site of FIG. 2A with a portion of the closure system of FIG. 1 deployed thereto.
Figure 3B:
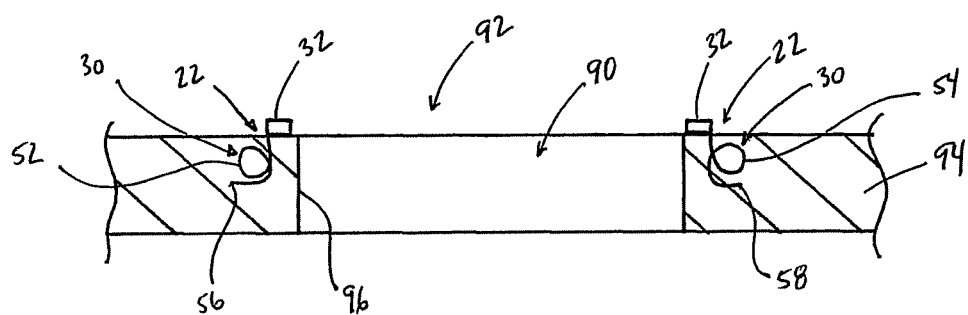
FIG. 3B is a cross-sectional view of the arrangement of FIG. 3A.

The system 20 described above can be employed to effectuate closure of a wide variety of internal bodily tissue openings. For example, FIGS. 2A and 2B schematically illustrate an opening 90 formed at a target site 92 of bodily tissue 94. The target site 92 can be virtually any internal bodily organ or other tissue structure (e.g., vessel), and in some embodiments is the ventricular apex of the heart. Regardless, and as shown in FIGS. 3A and 3B, the clip assemblies 22 are deployed about a perimeter 96 of the opening 90, with the ends 56, 58 piercing through the tissue 94, thereby embedding the self-closing clips 30 to the target site 92. While FIG. 3B reflects the leg segments 52, 54 as passing partially through a thickness of the tissue structure 94, with other techniques, one or both of the leg segments 52 and/or 54 of one or more of the self-closing clips 30 can pass through an entire thickness of the tissue structure 94 in securing the corresponding clip assembly 22 at the target site 92. Regardless, with embodiments in which the clip assemblies 22 include the coupling body 32 (or similar structure), the clip assembly 22 are arranged such that the corresponding coupling body 32 is laterally spaced from the immediately adjacent edge of the perimeter 96 for reasons made clear below.

Figure 4:
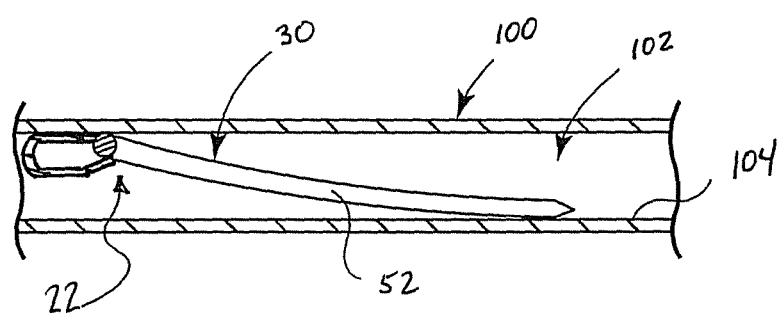
FIG. 4 is a simplified, cross-sectional view of a delivery device useful in delivering the closure system of FIG. 1.

Deployment of the clip assemblies 22 at the target site 92 can be accomplished in a variety of fashions, some of which are described in greater detail below. In more general terms, the self-closing clips 30 are initially presented to the target site 92 in a deflected state in which the leg segments 52, 54 are forced to a more straightened shape or configuration. For example, as generally shown in FIG. 4, a delivery device 100 (e.g., rigid or semi-rigid tube or catheter) forces the leg segments 52, 54 (one of which is shown in FIG. 4) to the deflected state in a manner permitting sliding movement of the self-closing clip 30 along a passageway 102 defined by the delivery device 100. The legs 52, 54 bear against an inner surface 104 of the delivery device 100, forcing the legs 52, 54 to a substantially straightened state. Upon being released from the confines of the delivery device 100 (e.g., via a longitudinal or radial opening to the passageway 102), the clip 30 automatically self-reverts or self-transitions from the deflected state of FIG. 4 to or toward the natural, undeflected state shown in FIG. 1. With this general construction in mind, then, the delivery device 100 is initially loaded with the clip assemblies 22 (e.g., the clip assemblies 22 are arranged end-to-end along a length of the passageway 102). Optionally, the flexible tether 24 is pre-threaded to the clip assemblies 22, and thus is also loaded within the delivery device 100. The delivery device 100 is then deployed to the target site 92. The clip assemblies 22 are sequentially, or in other embodiments simultaneously, released from the delivery device 100. As the so-released self-closing clip 30 transitions toward the natural state, then, the ends 56, 58 pierce through the tissue 94 (e.g., the epicardial surface), effectuating attachment to the target site 92.

Figure 5A:
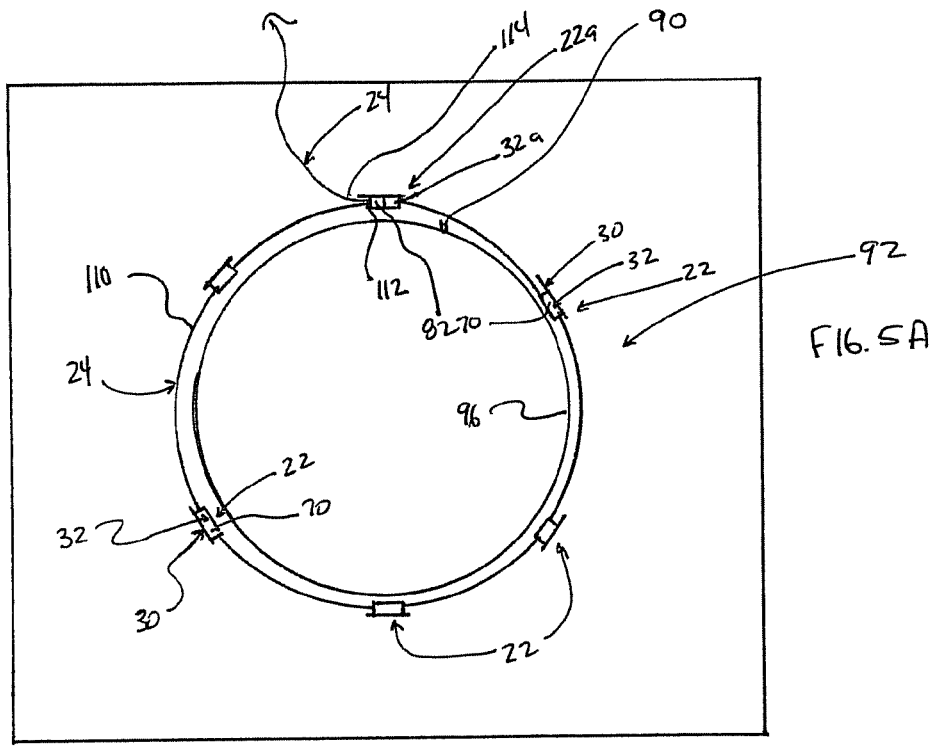
FIG. 5A is a simplified plan view of the target site of FIG. 2A along with the closure system of FIG. 1 fully deployed.

As shown in FIG. 5A, the tether 24 is coupled to the self-closing clips 30, for example via the optional coupling bodies 32. In this regard, the clip assemblies 22 can first be deployed to the target site 92 prior to coupling of the flexible tether 24 (e.g., the flexible tether 24 is threaded through the clasp 70 after the clip assemblies 22 have been secured to the target site 92). Alternatively, the flexible tether 24 can be coupled to the clip assemblies 22 prior to deployment (e.g., the clip assemblies 22 can be loaded within the delivery device 100 (FIG. 4) with the flexible tether 24 already captured or threaded within the corresponding clasps 70). With embodiments in which the coupling body 32 is not provided, the flexible tether 24 can be wound about the intermediate segment 50 (FIG. 1) of each of the clips 30, or otherwise directly connected thereto (e.g., the intermediate segment 50 can form a bore through which the flexible tether 24 is threaded).

Figure 5B:
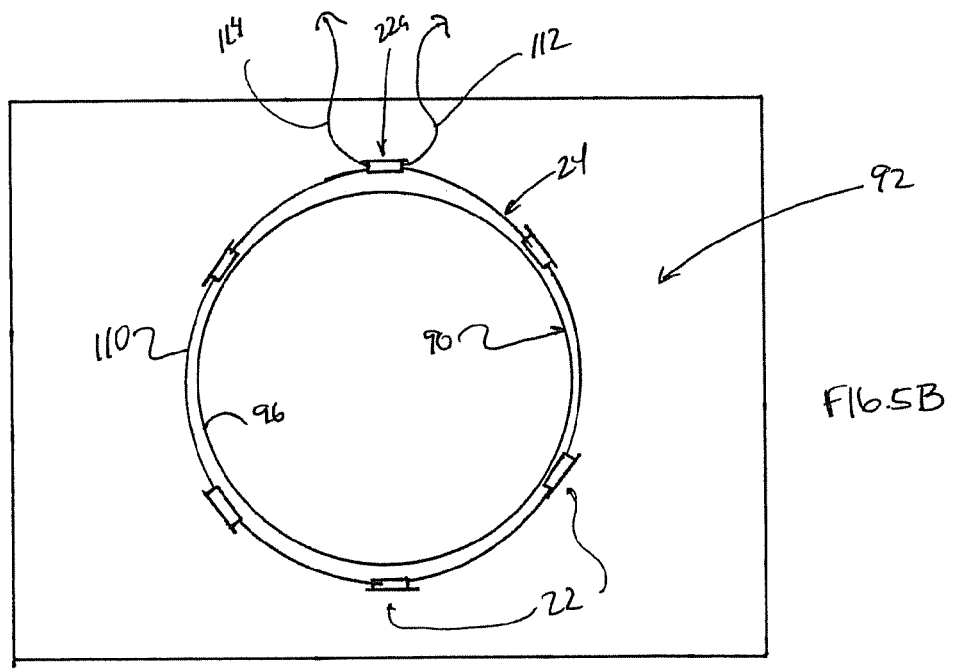
FIG. 5B is another view of the target site of FIG. 2A with the closure system of FIG. 1 deployed thereto in a different arrangement in accordance with principles of the present disclosure.
Figure 6A:
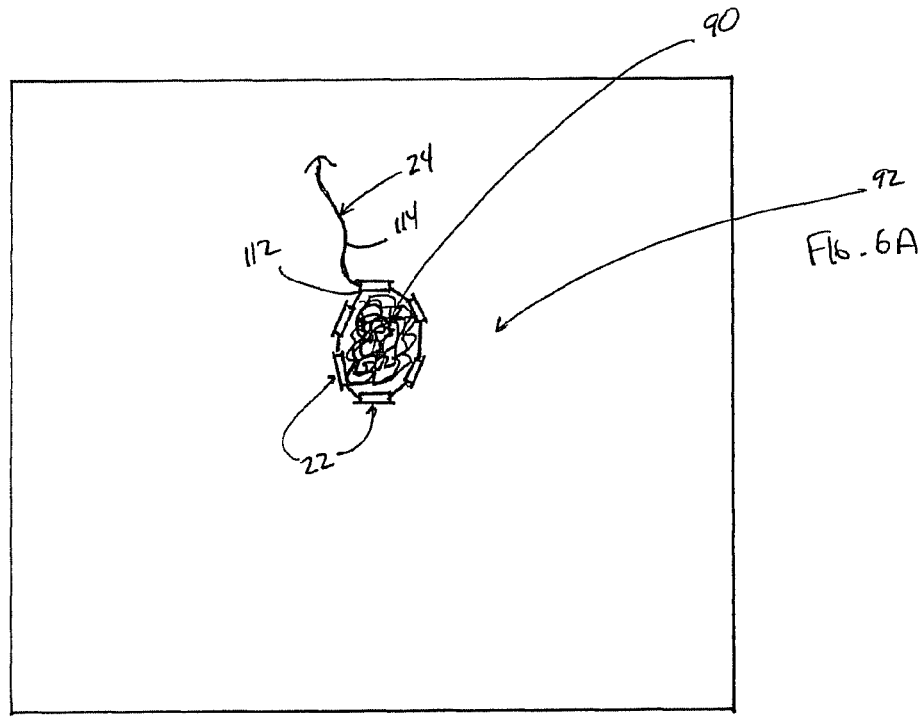
FIGS. 6A and 6B illustrate use of the closure system of FIG. 1 in closing the opening of FIG. 2A.
Figure 6B:
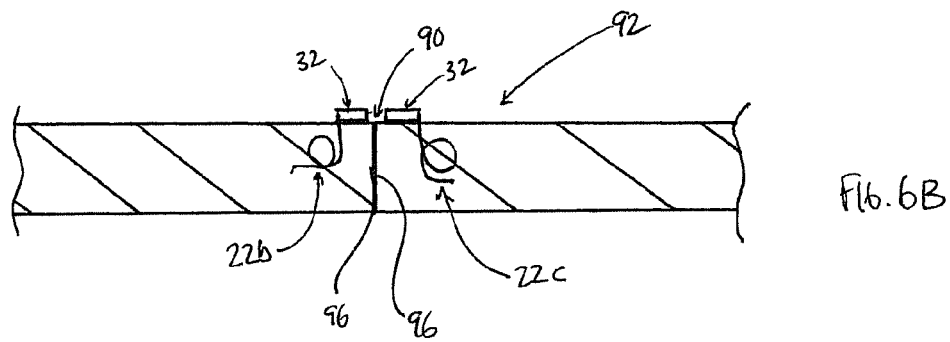

Regardless, upon deployment of the clip assemblies 22 and coupling of the flexible tether 24, the flexible tether 24 forms a loop 110 extending about or encompassing the perimeter 96 of the opening 90. The loop 110 terminates at opposing loop ends 112, 114 that are otherwise connected to the first clip assembly 22a. With the arrangement of FIG. 5A, the first loop end 112 is affixed to the first clip assembly 22a (via the second portion 82 of the coupling body 32a), whereas the second loop end 114 extends proximally from the first clip assembly 22a. Alternatively, and as shown in FIG. 5B, both of the loop ends 112, 114 can extend from the first clip assembly 22a. Regardless, the flexible tether 24 is slidably yet rigidly interconnected between the clip assemblies 22. Thus, when a pulling force is applied to one or both of the loop ends 112 and/or 114, this pulling force is transposed onto the embedded clip assemblies 22, thereby drawing the perimeter 96 of the opening 90 onto itself, thus closing the opening 90 as shown in FIGS. 6A and 6B. As best reflected in FIG. 6B, by arranging the clip assemblies 22 such that the coupling body 32 (where provided) is laterally spaced from the corresponding proximate edge of the opening 90, sufficient spacing exists between the coupling bodies 32 of oppositely-located clip assemblies 22 (e.g., the clip assemblies 22b, 22c identified in FIG. 6B) to permit intimate contact of the tissue 94 upon itself with tightening of the flexible tether 24. In other words, arrangement of the clip assemblies 22 is sufficient to permit complete closure of the opening 90 in the closed state of FIGS. 6A and 6B. The loop ends 112, 114 (FIG. 6A) are then secured (e.g., a knot is formed in the flexible tether 24) so as to maintain the target site 92 in the closed state.

As indicated above, but one potential internal bodily opening that can be treated by the closure system 20 is a transapical access opening. Similar openings requiring post-procedure closure arise in many other surgical contexts, such as natural orifice transluminal endoscopic surgery (NOTES). NOTES can be utilized in various bodily regions (e.g., gastric, vaginal, etc.), and generally entails forming a surgical incision through a bodily structure (e.g., gastric incision) through which subsequent procedures are performed. The closure system 20 can be employed as part of these procedures to close the incision (e.g., closure of the gastric incision or vaginal incision). Along these same lines, methods in accordance with the present disclosure also include deploying the closure system 20 to the closure of the gallbladder stump in cholecystectomy, or internal plication of the bowel. Tubal ligation (trans-vaginal) is also contemplated.

Figure 7A:
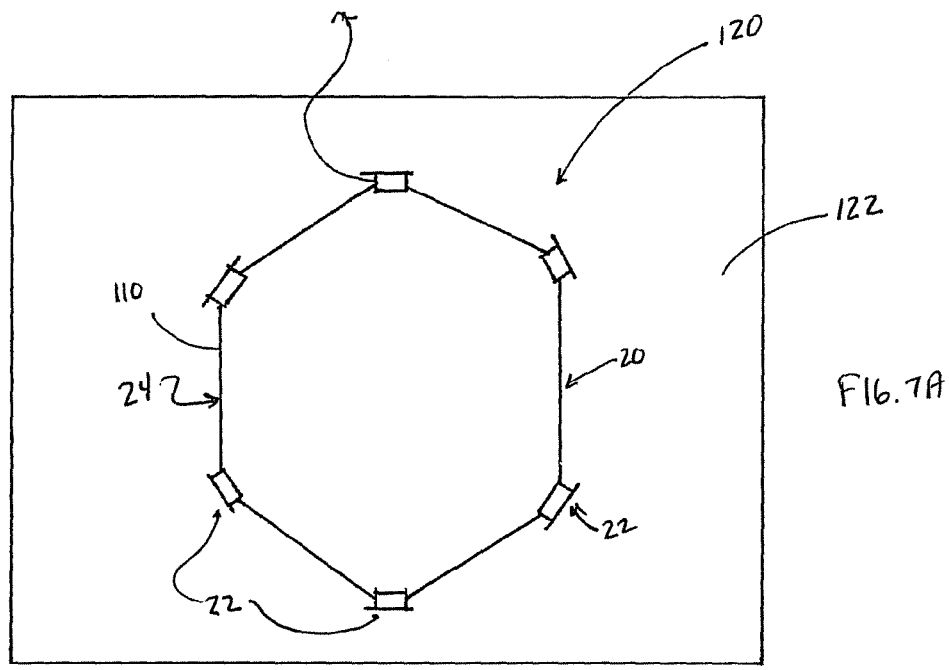
FIGS. 7A-7C illustrate another application of the closure system of FIG. 1 in closing an opening at a target site.

While the above methodologies entail deployment of the closure system 20 about a previously formed opening, in other embodiments, the system 20 is deployed prior to formation of the opening. For example, FIG. 7A generally illustrates another internal bodily target site 120, at least a portion of which consists of bodily tissue 122. In accordance with other embodiments of the present disclosure, the clip assemblies 22 and the flexible tether 24 are initially deployed to the target site 120 as described above, except that an opening has not yet been formed at the target site 120. For example, as part of a trans-apical access procedure (e.g., deployment of a transcatheter prosthetic heart valve), the clip assemblies 22 and the tether 24 can be deployed prior to forming the trans-apical access opening in the wall of the ventricular apex. Once again, the clip assemblies 22 maintain the flexible tether 24 to define the loop 110.

Figure 7B:
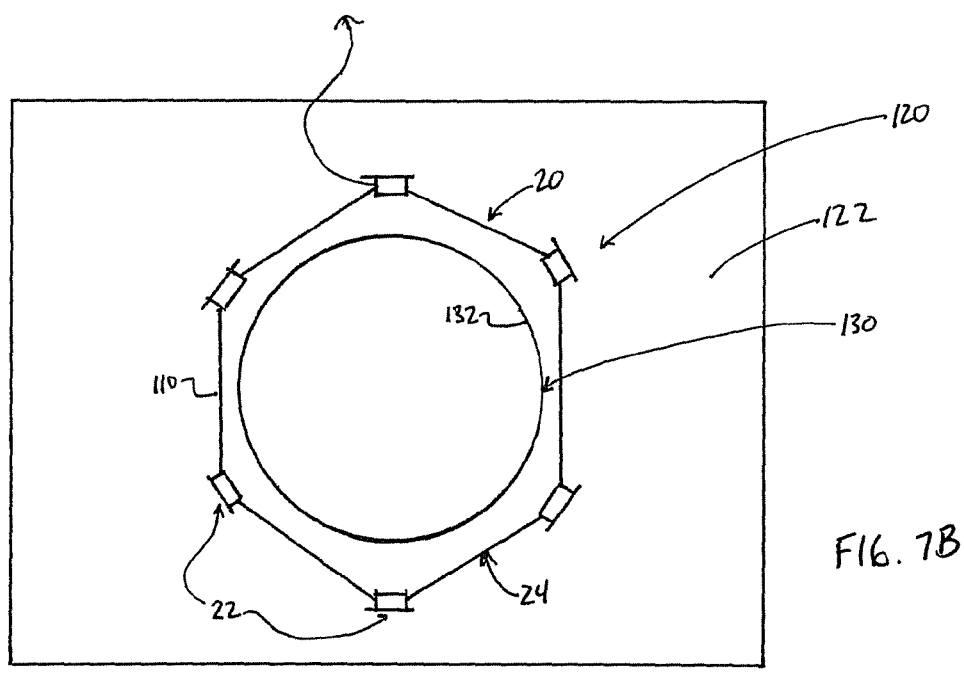
Figure 7C:
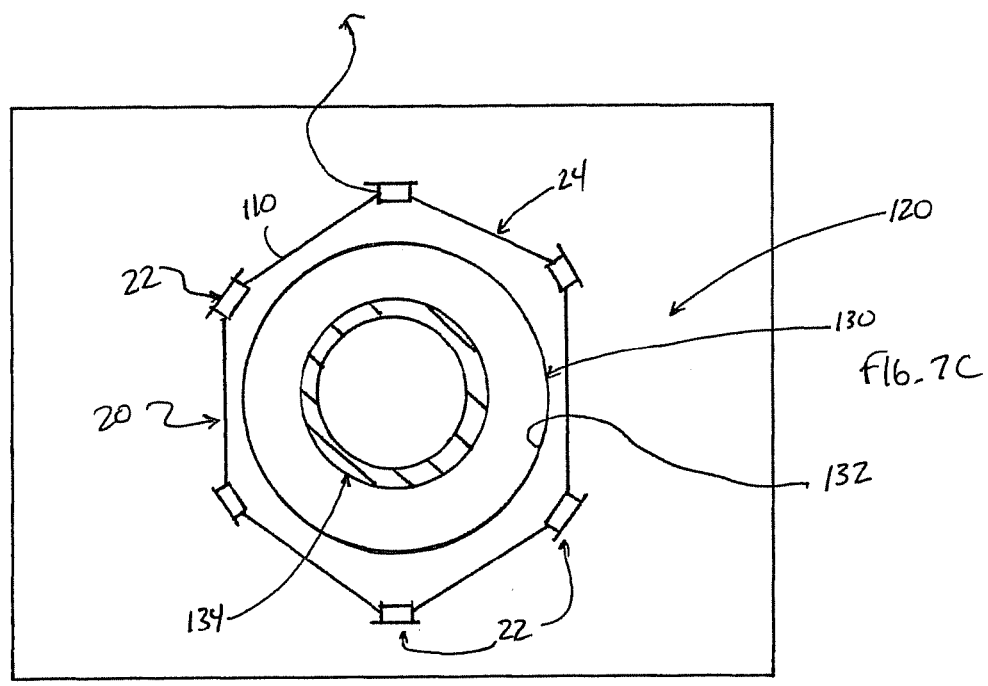

As shown in FIG. 7B, an opening or orifice 130 (e.g., a trans-apical access opening) is then formed at the target site 120, with a perimeter 132 of the opening 130 being entirely within or circumscribed by the loop 110. Subsequent procedures, as desired, can then be performed through the opening 130. For example, where the closure system 20 is used in connection with a trans-apical valve delivery procedure, a delivery catheter or other instrument can be inserted through the opening 130. One such instrument 134 is shown generally in FIG. 7C. Upon completion of the desired procedures (e.g., implantation of a heart valve repair device), the instrument 134 is removed from the opening 130, and the closure system 20 operated to close and secure the opening 130 as described above.

Figure 7D:
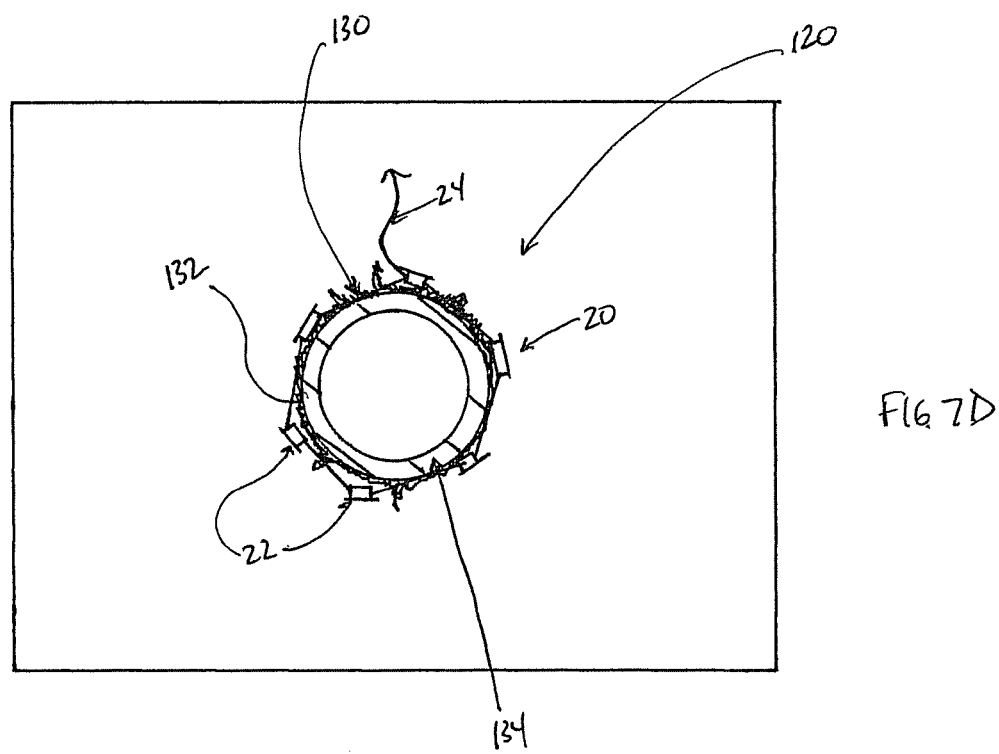
FIG. 7D illustrates another application of the closure system of FIG. 1 in maintaining an instrument at a target site.

In yet other, related embodiments, the closure system 20 can be operated to support the instrument 134 while deployed within the opening 130. For example, as shown in FIG. 7D, with the instrument 134 disposed within the opening 130, the flexible tether 24 can be tightened, thereby drawing the clip assemblies 22, and thus the tissue portions attached thereto, toward the instrument 134. In particular, the perimeter 132 of the opening 130 is plicated, and brought into contact with an outer surface 136 of the instrument 134. The flexible tether 24 can be temporarily maintained in this partially-closed state, thereby stabilizing the instrument 134 relative to the target site 120/opening 130. When removal of the instrument 134 is desired, the flexible tether 24 can be loosened, thereby allowing the opening 130 to expand in a manner permitting easy removal of the instrument 134.

In yet other embodiments, the instrument 134 is intended to be permanently maintained at the target site 120. Under these circumstances, the closure system 20 is operated as described above, with the tissue 122 of the target site 120 and the instrument 134 forming a sealed closure at the target site 120. For example, some methods in accordance with principles of the present disclosure relate to the implantation of a cardiac stimulation device (e.g., pacemaker or ICD) in which a stimulation-applying lead body (e.g., the instrument 134) is delivered to the heart via a transthorasic transatrial approach, with the lead 134 extending through, and being permanently maintained at, a punctured opening 130 in the right atrium 120. Alternatively, the lead 134 can be delivered via an internal jugular vein approach in which the lead 134 is delivered through an opening 130 formed through a wall of the internal jugular vein 120. Under these and other circumstances, the closure system 20 of the present disclosure can be employed to effectuate long-term sealing of the tissue in question about the deployed electrical lead (or other instrument).

Yet another useful application of the closure system 20 in accordance with principles of the present disclosure relates to repair of a paravalvular leak. As a point of reference, some techniques for effecting heart valve replacement or repair (e.g., mitral or tricuspid valve) entails implanting a prosthetic heart valve (or stented heart valve repair device) to the native heart valve annulus. One such arrangement is generally reflected in FIG. 8A that otherwise depicts a valve prosthesis 150 implanted to a native heart valve annulus 152. In some instances, for example due to differences between a shape of the prosthesis 150 and a shape or geometry of the annulus 152, one or more openings 154 (or "leaks") are formed.

Figure 8B:
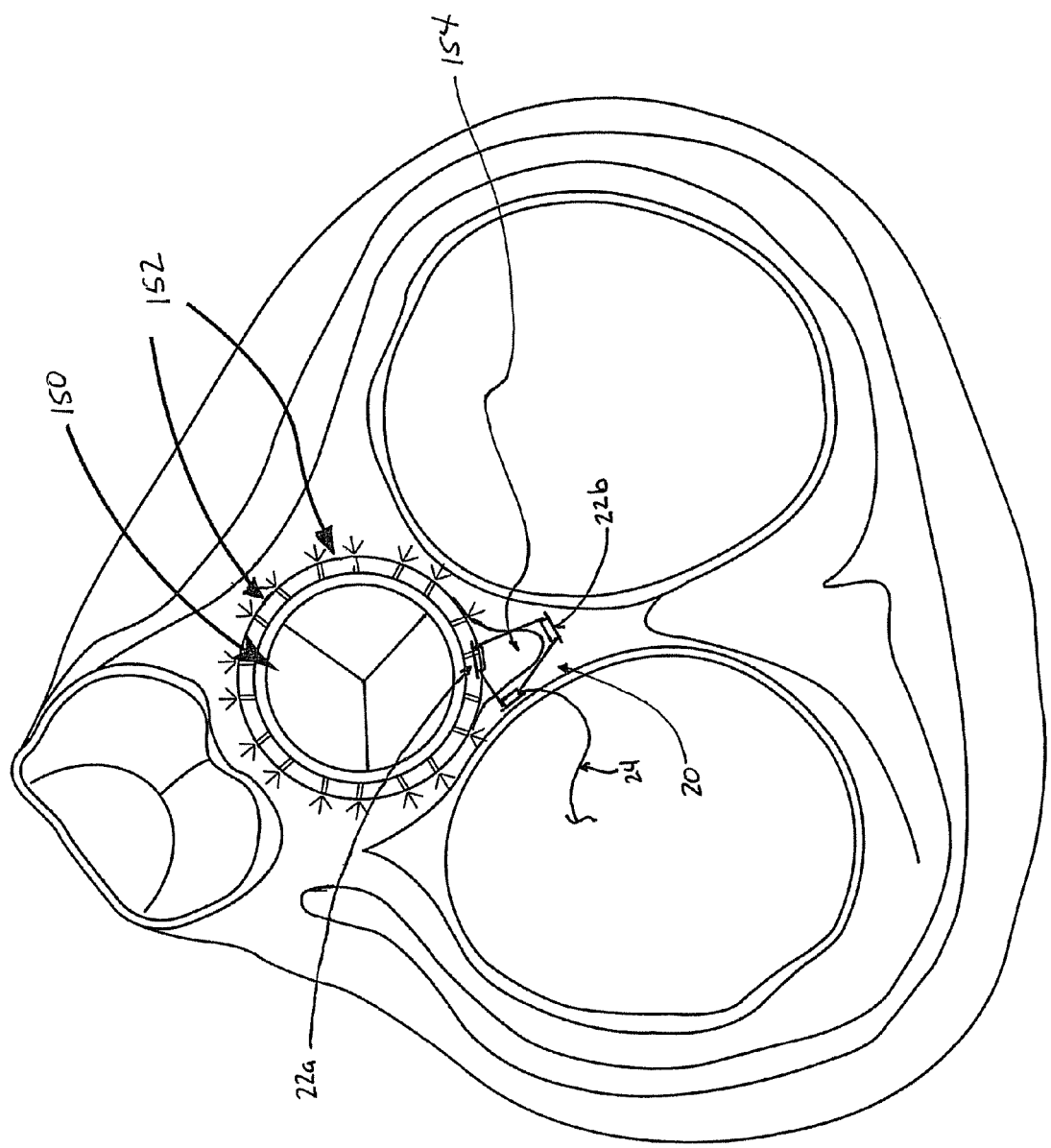
FIG. 8B illustrates deployment of the closure system of FIG. 1 to the target site of FIG. 8A.
Figure 8C:
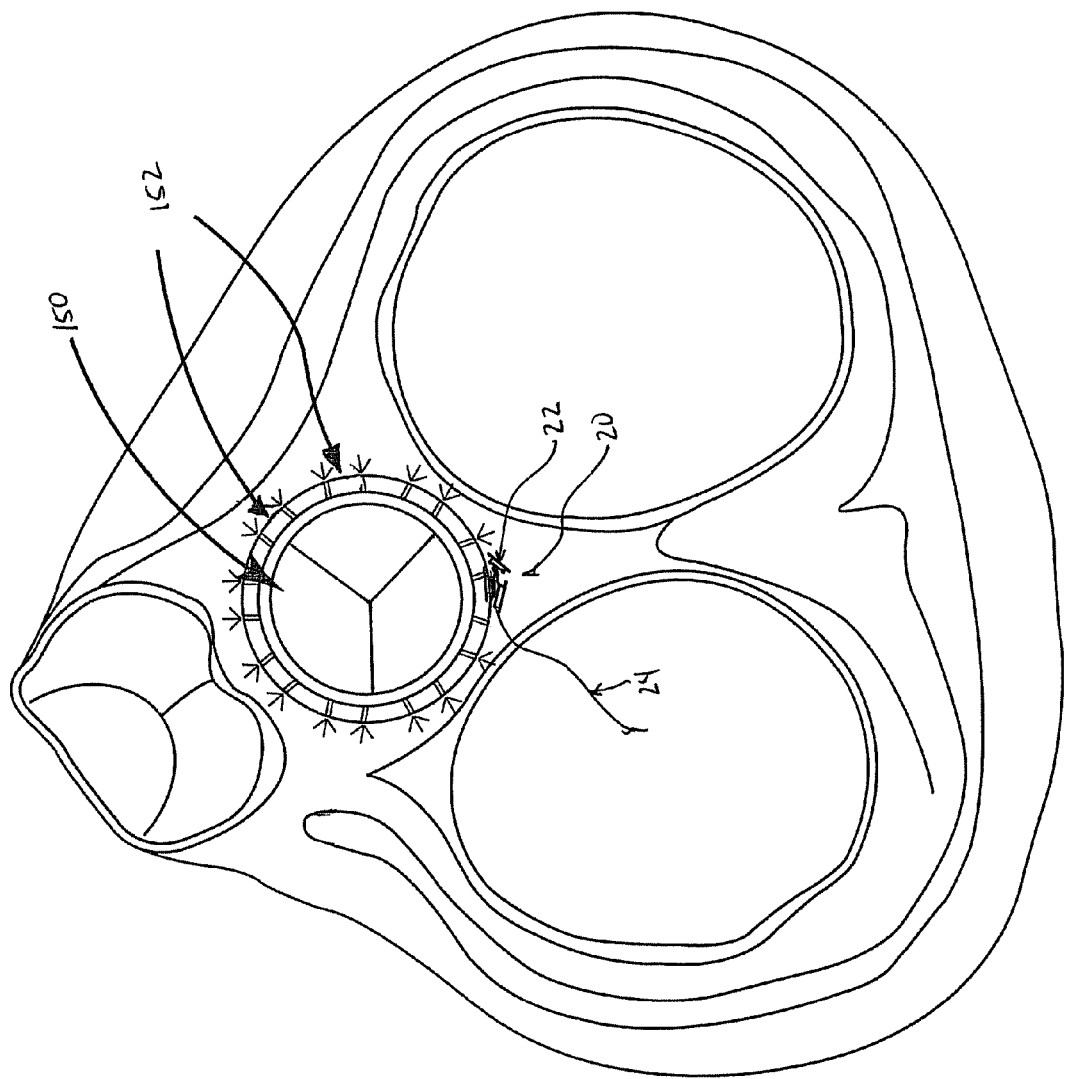
FIG. 8C illustrates operation of the closure system of FIG. 8B in closing the paravalvular leak associated with the target site of FIG. 8A.

With the above in mind, the closure system 20 can be employed to close the paravalvular opening 154. In particular, and as shown in FIG. 8B, the closure system 20 is deployed as generally described above, for example via catheter or similar device, with the clip assemblies 22 being attached to one of the prosthesis 150 or the annulus 152. For example, FIG. 8B illustrates a first one of the clip assemblies 22a attached to a structure of the prosthesis 150, whereas a second one of the clip assemblies 22b is attached to the tissue of the native annulus 152. With tightening of the flexible tether 24, the prosthesis 150 and the annulus tissue 152 are drawn toward one another, thus closing the paravalvular opening 154 as shown in FIG. 8C.

Yet other techniques envisioned by the present disclosure for closing the paravalvular opening 154 include deployment of a homogenous plug body 160 within the opening 154 as shown in FIG. 8D, along with one or more of the self-closing clips 30 described above that holds the plug body 160 in place. The plug body 160 can have a variety of constructions (e.g., sponge, Dacron, foam bag, etc.), and provides long-term occlusion of the paravalvular opening 154.

Figure 9A:
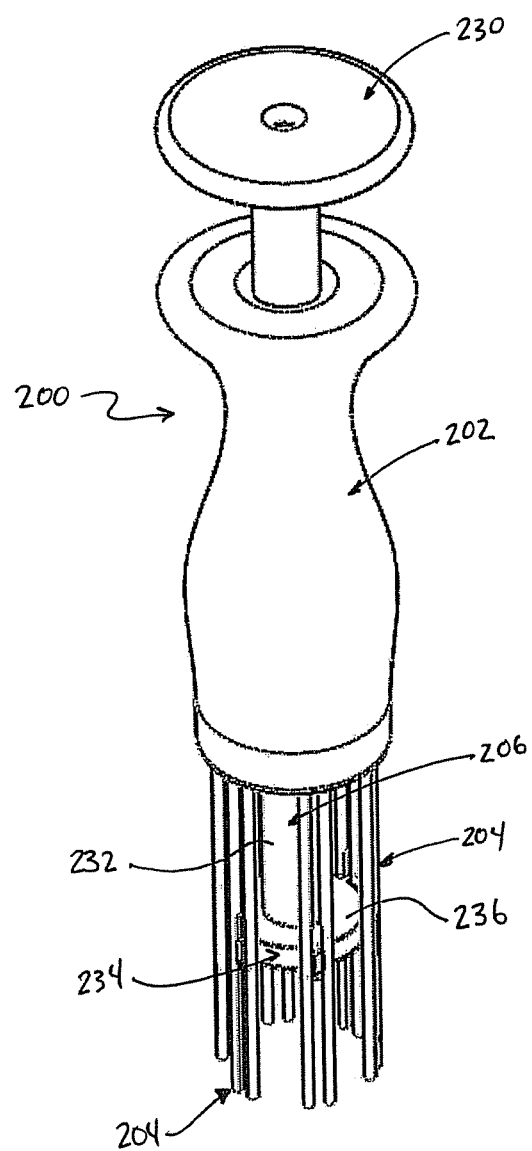
FIG. 9A is a perspective view of a delivery tool useful in deploying the closure system of FIG. 1 in an initial state.
Figure 9B:
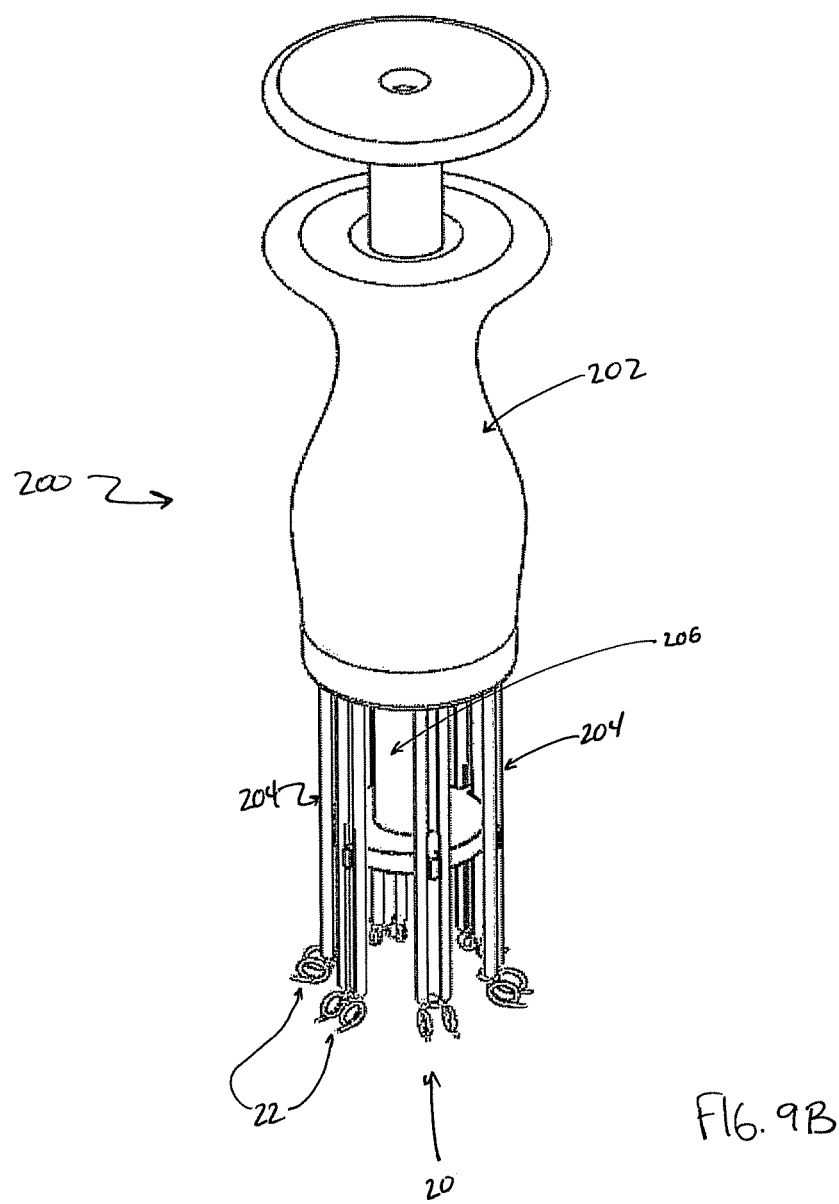
FIG. 9B is a perspective view of the delivery tool of FIG. 9A in a deployment state.

As mentioned above, the closure system 20 can be delivered to an internal bodily target site in a variety of manners, for example percutaneous (e.g., via catheter), minimally invasive, or open surgical setting. Further, the delivery tools employed can be configured to deploy the clip assemblies 22 sequentially/individually. Alternatively, with other systems in accordance with the present disclosure, the delivery tool can be configured to substantially simultaneously deploy a plurality of the clip assemblies 22. For example, FIGS. 9A and 9B illustrate a delivery tool 200 useful for delivering and deploying the closure system 20. More particularly, in an initial state (FIG. 9A), the delivery tool 200 maintains the clip assemblies 22 (hidden in FIG. 9A) in the deflected state described above. Upon actuation of the delivery tool 200 to a deployment state (FIG. 9B), the clip assemblies 22 are released from the delivery tool 200 in a substantially simultaneous manner, and self-revert to the natural state to engage tissue and/or other structures at a target site.

The delivery tool 200 can assume various forms, and generally consists of a handle 202, a plurality of retention assemblies 204, and an actuator assembly 206. The retention assemblies 204 and the actuator assembly 206 are maintained by the handle 202, with the clip assemblies 22 being slidably maintained by respective ones of the retention assemblies 204. Further, the actuator assembly 206 interfaces with each of the clip assemblies 22 as loaded within the retention assemblies 204. With this arrangement, movement of the actuator assembly 206 is transposed on to the loaded clip assemblies 22, causing the clip assemblies 22 to move or slide within the corresponding retention assemblies 204, and ultimately resulting in release or deployment of the clip assemblies 22 from the delivery tool 200.

Figure 10:
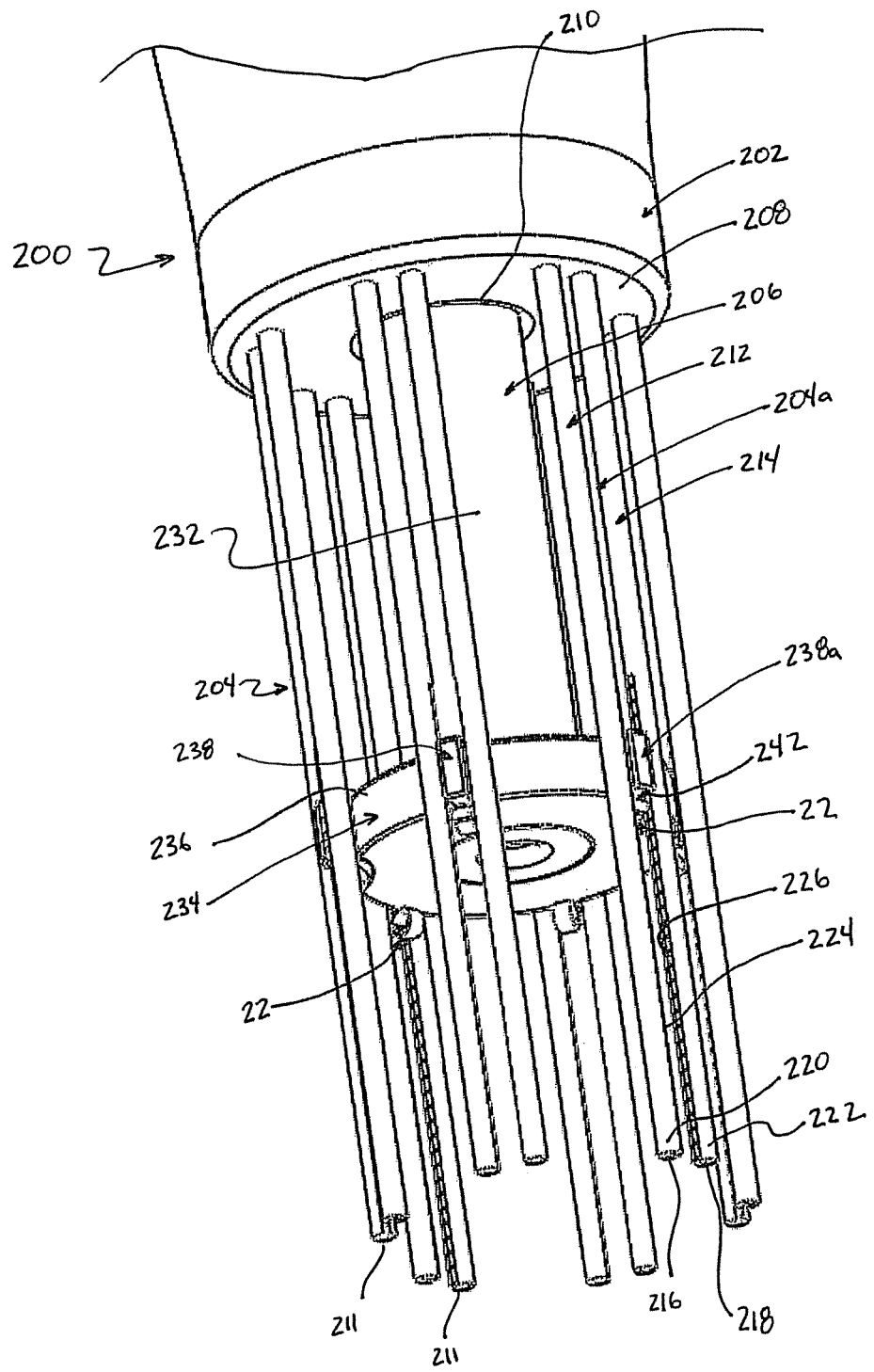
FIG. 10 is a bottom perspective view of portion of the delivery tool of FIG. 9A.

The handle 202 is, in general terms, sized to be grasped by a user's hand, and incorporates various features for interfacing with the retention assemblies and the actuator assembly 206. For example, as best shown in FIG. 10, the handle 202 includes or forms a base 208 adapted to retain the retention assemblies in a spaced apart, generally circular arrangement. The base 208 further forms a central bore 210 within which a portion of the actuator assembly 206 is slidably received. Though not shown, the handle 202 can include additional internal features that assist in promoting controlled, axial sliding of the actuator assembly 206 relative to the bore 210.

The retention assemblies 204 extend from the handle 202 to a distal side 211 and, in some embodiments, are identical. The retention assemblies 204 can each include opposing, first and second tubes 212, 214. For example, with respect to the retention assembly 204a identified in FIG. 10, the tubes 212, 214 each form a lumen 216, 218 that is open at a corresponding distal end 220, 222 (otherwise corresponding with the distal side 211). Further, the tubes 212, 214 each form a longitudinal slot 224, 226, respectively, that extends to the distal end 220, 222 and is radially open to the corresponding lumen 216, 218. The tubes 212, 214 are arranged such that the longitudinal slots 224, 226 face one another, with a lateral spacing between the tubes 212, 214 corresponding with a dimension of the clip assembly 22 (referenced generally in FIG. 10) retained thereby.

Figure 11:
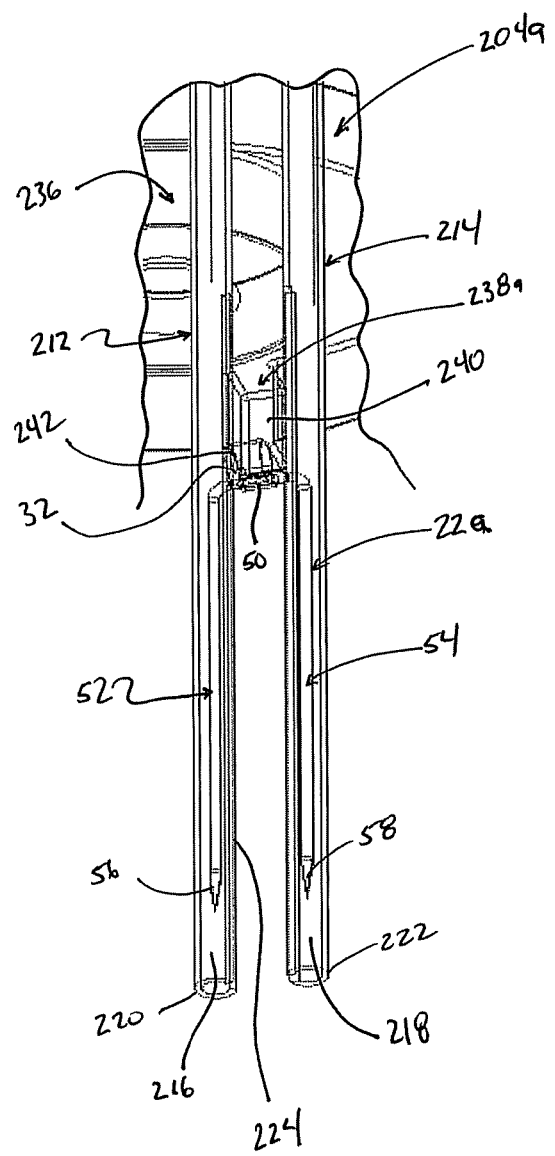
FIG. 11 is an enlarged view of a portion of the delivery tool of FIG. 9A.

FIG. 11 illustrates in greater detail a relationship of the clip assembly 22a relative to the retention assembly 204a in the initial state. As a point of reference, although the clip assembly 22a is shown as being fully visible in the view of FIG. 11 for ease of explanation, in actual practice, a majority of the clip assembly 22a will be hidden within the tubes 212, 214. The first leg segment 52 is disposed within the lumen 216 of the first tube 212, with the first tube 212 sized and sufficiently rigid to force or deflect the first leg segment 52 to a substantially straightened shape as shown. A width of the longitudinal slot 224 is less than a diameter of the first leg segment 52 such that the first leg segment 52 is slidably captured within the lumen 216. The second leg segment 54 is similarly slidably captured within the lumen 218 of the second tube 214. The intermediate segment 50 extends between the first and second tubes 212, 214, projecting through the corresponding longitudinal slot 224, 226, with the coupling body 32 (where provided) being partially located within the lateral spacing between the tubes 212, 214. With this arrangement, the clip assembly 22a can be moved in a distal direction, with the first leg segment 52 sliding within the first tube 212, the second leg segment 54 sliding within the second tube 214, and the intermediate segment 50/coupling body 32 sliding between the first and second tubes 212, 214.

Returning to FIG. 10, the retention assemblies 204 are arranged in a generally circular pattern relative to a central axis of the delivery tool 200. Other shapes or arrangements of the retention assemblies 204 are also envisioned. Further, while FIG. 10 illustrates six of the retention assemblies 204, the delivery tool 200 can alternatively incorporate any other number, greater or lesser, corresponding with the desired number of clip assemblies 22 to be deployed. Regardless, the retention assemblies 204 combine to define a collective perimeter that is selected to correspond with, but be slightly greater than, a size of the target site opening (not shown) to be closed.

With reference to FIGS. 9A and 10, the actuator assembly 206 generally includes, in some constructions, a grip 230, a shaft 232, and a plate 234. The grip 230 is sized to be conveniently grasped by a user's hand, with the shaft 232 extending distally from the grip 230. The plate 234, in turn, extends from the shaft 232 opposite the grip 230, and incorporates features for interfacing with the clip assemblies 22 as described below.

The shaft 232 has an outer diameter corresponding with a diameter of the bore 210, and defines the central axis of the delivery tool 200. More particularly, the shaft 232 is sized and configured to be slidably retained by the handle 202.

The plate 234 extends radially from the shaft 232, and includes a plate body 236 and a plurality of fingers 238. An outer dimension (e.g., diameter) of the plate body 236 corresponds with, or is slightly less than, the collective perimeter (e.g., collective diameter) defined by the retention assemblies 204. As best shown in FIG. 10, then, the plate body 236 can radially support the retention assemblies 204, but is longitudinally slidable relative thereto. The fingers 238 project radially from the plate body 236, and are circumferentially spaced from one another in accordance with a spacing between the retention assemblies 204. In other words, one of the fingers 238 is associated with each one of the retention assemblies 204, respectively. In this regard, a width of each finger 238 corresponds with, and is slightly less than, a lateral spacing between the first and second tubes 212, 214 of the corresponding retention assembly 204.

A relationship between one of the fingers 238a and one of the retention assemblies 204a is further reflected in FIG. 11. As shown, the finger 238a is disposed between the first and second tubes 212, 214, with the width of the finger 238a permitting the finger 238a to freely slide between the tubes 212, 214. Radial projection of the finger 238a from the plate body 236 terminates at a leading side 240 that is proximate an exterior surface of the tubes 212, 214. Further the finger 238a defines a lower bearing surface 242 (referenced generally in FIG. 11, and identified more clearly in FIG. 10). The bearing surface 242 is adapted to selectively interface with the corresponding clip assembly 22a during movement of the actuator assembly 206 as described below, and can optionally incorporate features that promote temporary engagement with the clip assembly 22a.

Prior to use, the delivery tool 200 is loaded with at least the clip assemblies 22. More particularly, the actuator assembly 206 is retracted relative to the retention assemblies 204 as shown in FIG. 9A, with the plate 234 proximally spaced from the distal side 211. Individual ones of the clip assemblies 22 are loaded within respective ones of the retention assemblies 204, and thus transitioned to the deflected (e.g., substantially straightened) state. In this regard, the optional coupling body 32 associated with each of the clip assemblies 22 is located radially inwardly. Where desired, the flexible tether 24 (FIG. 1) can be pre-loaded to the clip assemblies 22, and thus also maintained by the delivery tool 200. In the initial state, the actuator assembly 206 can be maneuvered such that the plate body 236 contacts the coupling body 32 of each of the clip assemblies 22, and the fingers 238 contact respective ones of the clip assemblies 22 as shown in FIG. 10. With further reference to FIG. 11, for example, the plate 234 is sufficiently proximally spaced from the distal ends 220, 222 such that the piercing ends 56, 58 of the clip assembly 22a are within the corresponding lumens 216, 218. The bearing surface 242 is in abutting contact with the intermediate segment 50 of the clip assembly 22 that otherwise extends between the tubes 212, 214.

Figure 12:
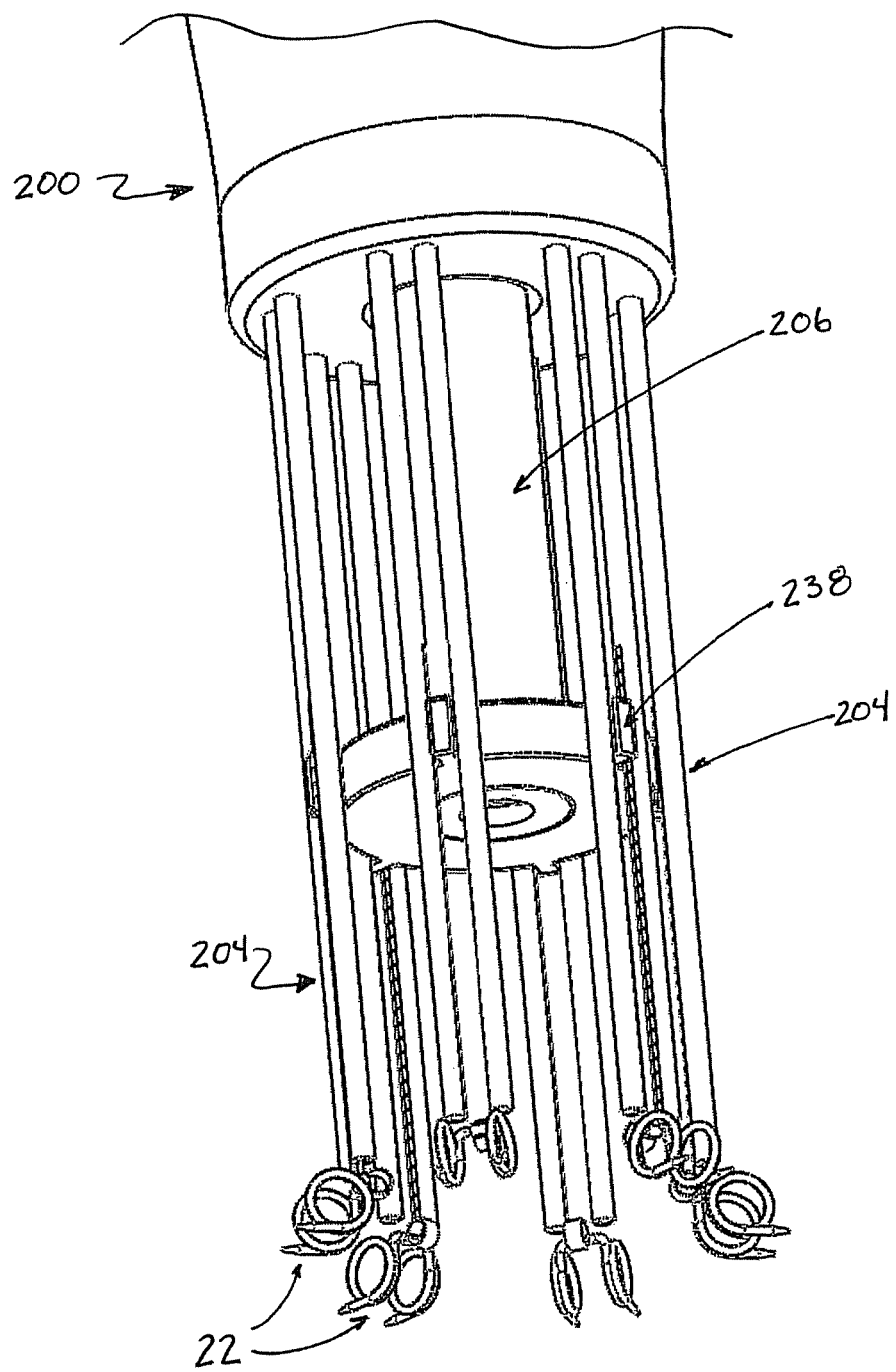
FIG. 12 is an enlarged, perspective view of a portion of the delivery tool of FIG. 9A in deploying the closure system of FIG. 1.

During use, the delivery tool 200 is delivered to the target site, and the retention assemblies 204 positioned about the opening (not shown) to be closed (or at the desired location at which the opening will subsequently be formed). For example, the distal ends 220, 222 of each of the tubes 212, 214 are placed in close proximity, or into contact, with the tissue or other structure(s) of the target site that otherwise immediately surround the opening. The user then operates the actuator assembly 206, causing the shaft 232/plate 234 to slide distally. This distal motion is transferred onto the clip assemblies 22 via the abutting interface between the clip assemblies 22 and the corresponding fingers 238, such that the clip assemblies 22 slide within the corresponding retention assembly 204. Distal movement of the clip assemblies 22 relative to the retention assemblies 204 continues until the clip assemblies 22 are released or deployed from the tubes 212, 214 as shown in FIG. 12. In connection with this deployment, the clip assemblies 22 self-transition back toward the natural state as described above.

It will be understood that the delivery tool 200 is but one acceptable example of a device useful in deploying the closure system 20 of the present disclosure. For example, the delivery tool 200 can be modified to incorporate a catheter-like construction (e.g., as described in U.S. application Ser. No. 12/401,183). The device can assume other forms that also promote substantially simultaneous deployment of the clip assemblies 22. Conversely, and as described elsewhere, the device employed to deliver the clip assemblies 22 can be configured to deploy the clip assemblies 22 on a sequential basis, and thus can be of a reduced size as compared to the delivery tool 200 (e.g., akin to a catheter).

Although the present disclosure has been described with reference to preferred embodiments, workers skilled in the art will recognize that changes can be made in form and detail without departing from the spirit and scope of the present disclosure.

What is claimed is:

1. A method for closing an opening at a target site including bodily tissue, the method comprising:
   embedding a plurality of clips into the target site in a spaced apart manner about a perimeter of the opening, each clip being U-shaped and having two substantially straight parallel legs connected by an intermediate section extending between the legs, the legs and the intermediate section defining a first plane, and a substantially rigid coupling body which is configured to slidably capture a flexible tether and is assembled to and extends radially inward from the first plane of the legs and the intermediate section, at least one coupling body comprising a first portion through which the tether is slidably captured and a second portion shaped differently than the first portion and thereby configured to optionally attach a distal end of the tether or slidingly capture the tether, each leg having a pointed tip such that upon release from a delivery tool, each leg is embedded into the bodily tissue by self-transitioning from substantially straight to curved, during which self-transitioning each of the two ends legs forms an overlapping loop around an axis which remains parallel to a second plane containing the perimeter, the legs maintaining an essentially constant distance between each other; and in the natural state, each pointed tip is directed radially outward while lying below and being generally parallel to the second plane containing the perimeter;
   coupling the flexible tether to the coupling body of each of the embedded clips along an axis of the coupling body which is displaced radially inwardly from the first plane of each clip to form a loop about an entirety of the perimeter of the opening, the loop terminating at opposing loop ends;
   applying a pulling force onto at least one of the opposing loop ends;
   wherein the pulling force along the radially inwardly displaced axis of the coupling body is transposed onto the embedded clips to draw the perimeter of the opening onto itself to completely close the opening in transitioning the target site from an open state to a closed state; and
   securing the opposing loop ends to maintain the target site in the closed state.

2. The method of claim 1, wherein the target site is apical cardiac tissue.

3. The method of claim 2, wherein the method is performed as part of a trans-apical access procedure.

4. The method of claim 3, wherein the method further includes:
   inserting a surgical tool through the opening prior to the step of transitioning the target site to a closed state.

5. The method of claim 4, wherein inserting a surgical tool includes:
   delivering a catheter through the opening;
   deploying a prosthetic heart valve through the catheter;
   implanting the prosthetic heart valve to a native annulus; and
   withdrawing the catheter from the opening.

6. The method of claim 2, wherein embedding the plurality of clips includes:
   driving the clips into an epicardial surface of the apical cardiac tissue.

7. The method of claim 1, further comprising:
   deploying and withdrawing a surgical tool through the opening prior to the step of completely closing the opening.

8. The method of claim 1, wherein driving the clips includes:
   retaining the clips in a deflected state within the delivery tool; and
   releasing the clips from the delivery tool at the target site.

9. The method of claim 1, wherein an outer diameter of the second portion is less than a diameter of a passage of the first portion through which the tether is slidably retained, such that the tether extends about the second portion.

10. The method of claim 1, wherein the flexible tether is coupled to the clips prior to the step of embedding the plurality of clips at the target site.

11. The method of claim 10, further comprising:
    loading the plurality of clips and the coupled flexible tether into a catheter-based delivery tool prior to embedding the plurality of clips into the target site.

12. The method of claim 11, wherein embedding the plurality of clips includes:
    delivering a distal end of the catheter-based delivery tool on a minimally invasive basis to the target site.

13. The method of claim 12, wherein following the step of embedding the plurality of clips, at least one end of the flexible tether is accessible at a proximal end of the catheter-based delivery tool.

14. The method of claim 1, wherein the step of embedding the plurality of clips includes substantially simultaneously deploying the plurality of clips from the delivery tool.

15. The method of claim 1, wherein the target site includes a native heart valve annulus, and the opening is between the native annulus and an implanted prosthetic heart valve.

16. The method of claim 15, wherein embedding the plurality of clips includes:
    securing at least some of the clips to tissue of the native annulus; and
    securing at least some of the clips to a structure of the implanted prosthetic valve.

17. The method of claim 16, further comprising:
    percutaneously implanting the prosthetic heart valve to the native annulus.

18. The method of claim 1, wherein the method is performed as part of a natural orifice transluminal endoscopic surgery.

\* \* \* \* \*